(12) United States Patent
Conlan et al.

(10) Patent No.: US 9,931,436 B2
(45) Date of Patent: Apr. 3, 2018

(54) METHODS AND DEVICES TO STIMULATE THE FOLLICULAR NICHE USING ADIPOSE DERIVED REGENERATIVE CELLS AND ADIPOSE TISSUE

(71) Applicant: Kerastem Technologies LLC, Solana Beach, CA (US)

(72) Inventors: Bradford A. Conlan, Solana Beach, CA (US); Eric Daniels, La Jolla, CA (US)

(73) Assignee: Kerastem Technologies LLC, Solana Beach, CA (US)

( * ) Notice: Subject to any disclaimer, the term of this patent is extended or adjusted under 35 U.S.C. 154(b) by 99 days.

(21) Appl. No.: 14/611,898

(22) Filed: Feb. 2, 2015

(65) Prior Publication Data

US 2016/0220731 A1    Aug. 4, 2016

(51) Int. Cl.
*A61L 27/38*    (2006.01)

(52) U.S. Cl.
CPC ............................... *A61L 27/3834* (2013.01)

(58) Field of Classification Search
None
See application file for complete search history.

(56) References Cited

U.S. PATENT DOCUMENTS

2005/0208011 A1*  9/2005  Marko ..................... A61K 8/64
                                                              424/70.14
2007/0258956 A1   11/2007  Higgins et al.

FOREIGN PATENT DOCUMENTS

WO    2013133494 A1   9/2013
WO    2014207135 A1   12/2014

OTHER PUBLICATIONS

Fukuoka et al., The Latest Advance in Hair Regeneration Therapy Using Proteins Secreted by Adipose-Derived Stem Cells, The American Journal of Cosmetic Surgery vol., 29, No. 4, 2012.*
De Villiers et al., Adipose Derived Stem Cells and Smooth Muscle Cells: Implications for Regenerative Medicine, Stem Cell Rev and Rep (2009) 5: 256-265.*
Wu et al., The isolation and differentiation of human adipose-derived stem cells using membrane filtration, Biomaterials 33 (2012) 8228-8239.*
Zhu et al., Supplementation of Fat Grafts With Adipose-Derived Regenerative Cells Improves Long-Term Graft Retention, Annals of Plastic Surgery vol. 64, No. 2, Feb. 2010.*
Dini, M. et al., "Eyebrow regrowth in patient with atrophic scarring alopecia treated with an autologous fat graft," Dermatologic Surgery, 2014, vol. 40, No. 8, pp. 926-928.
Zanzoitera, F. et al., "Adipose derived stem cells and growth factors applied on hair transplantation. follow-up of clinical outcome," Journal of Cosmetics, Dermatological Sciences and Applications, 2014, vol. 4, pp. 268-274.
International Search Report for International Application No. PCT/US2016/015914, dated Aug. 19, 2016.
Written Opinion for International Application No. PCT/US2016/015914, dated Aug. 19, 2016.
International Preliminary Report on Patentability for International Application No. PCT/US2016/015914, dated Aug. 3, 2017.

* cited by examiner

*Primary Examiner* — Suzanne M Noakes
*Assistant Examiner* — Stephen M Chong
(74) *Attorney, Agent, or Firm* — Duane Morris LLP

(57) ABSTRACT

The present invention concerns a cell-enriched fat graft and methods of making and using the same. The present invention also provides a kit for making and using the cell-enriched fat graft of invention.

8 Claims, 3 Drawing Sheets

METHODS AND DEVICES TO STIMULATE THE FOLLICULAR NICHE USING ADIPOSE DERIVED REGENERATIVE CELLS AND ADIPOSE TISSUE

FIELD OF THE INVENTION

Embodiments disclosed herein generally relate to methods and devices to stimulate the follicular niche using adipose derived regenerative cells and adipose tissue and methods of making and using the same.

BACKGROUND OF THE INVENTION

Hair loss or baldness (technically known as alopecia) is a loss of hair from the head or body. Baldness can refer to general hair loss or androgenic alopecia (male pattern baldness). Some types of baldness can be caused by alopecia areata, an autoimmune disorder. The extreme forms of alopecia areata are alopecia totalis, which involves the loss of all head hair, and alopecia universalis, which involves the loss of all hair from the head and the body.

Baldness and hypotrichosis can have many causes, including fungal infection (tinea capitis), traumatic damage, such as by compulsive pulling (trichotillomania), as a result of radiotherapy or chemotherapy, and as a result of nutritional deficiencies such as iron, and as a result of autoimmune phenomena, including alopecia areata and hair loss associated with systemic lupus erythematosus.

A number of compositions and therapeutic methods are developed to address hair loss and to regrow hair, including medications such as Propecia and Rogaine, hair replacements, and hair restoration, with limited success.

Therefore, there is a need for additional approaches to prevent or ameliorate hair loss and hair regrowth.

The embodiments described below address the above identified issues and needs.

SUMMARY OF THE INVENTION

In one aspect of the present invention, it is provided a method for hair growth, which method comprising
  preparing a cell-enriched fat graft, and
  injecting into the subcutaneous space of an area of a subject in need thereof a cell-enriched fat graft to cause hair growth or cilia restoration or to prevent hair loss or cilia loss.

In some embodiments of the invention method, optionally in combination with any or all the various embodiments method disclosed herein, the cell-enriched fat graft comprises
  a) adipose stem and regenerative cells (ADRCs) and a fat tissue, or
  b) a platelet rich plasma and a fat tissue.

In some embodiments of the invention method, optionally in combination with any or all the various embodiments method disclosed herein, 1 gram of the cell-enriched fat graft comprises:
  ADRCs in a number ranging from about 10,000 cells to about 5 million cells, or
  the platelet rich plasma in a volume ranging from 0.001 mL to 0.9 mL.

In some embodiments of the invention method, optionally in combination with any or all the various embodiments method disclosed herein, the ADRCs and the fat tissue are provided in situ, and the cell-enriched fat graft is generated by mixing in-situ an amount of the ADRCs and an amount of the fat tissue prior to use.

In some embodiments of the invention method, optionally in combination with any or all the various embodiments method disclosed herein, the ADRCs are enzymatically extracted in situ from an adipose tissue, and the fat tissue is cleaned in situ.

In some embodiments of the invention method, optionally in combination with any or all the various embodiments method disclosed herein, the ADRCs are enzymatically extracted in situ and the fat tissue is collected and cleaned in situ from a liposuctioned tissue.

In some embodiments of the invention method, optionally in combination with any or all the various embodiments method disclosed herein, the area of a subject is ear drum or intestine.

In some embodiments of the invention method, optionally in combination with any or all the various embodiments method disclosed herein, preparing comprises:
  measuring the size of the area of the subject in need of hair growth or cilia restoration, determining a cell count in the cell-enriched fat graft,
  determining an amount of the cell-enriched fat graft of the cell count to generate effective hair growth or cilia restoration in the area.

In some embodiments of the invention method, optionally in combination with any or all the various embodiments method disclosed herein, the subject is a human being.

In another aspect of the present invention, it is provided a kit for providing a cell-enriched fat graft in situ, which kit comprising
  an adipose stem and regenerative isolation device; and
  an adipose tissue cleaning device,
  wherein the adipose stem and regenerative cells (ADRCs) isolation device comprises a mechanism to enzymatically extract ADRCs from an adipose tissue, and
  wherein the adipose tissue cleaning device comprises a mechanism to collect and clean an adipose tissue without causing injury to the adipose tissue.

In some embodiments of the invention kit, optionally in combination with any or all the various embodiments kit disclosed herein, the adipose tissue cleaning device comprises a soft bag comprising soft compartments.

In a further aspect of the present invention, it is provided a cell-enriched fat graft for hair growth or cilia restoration or prevention of hair loss or cilia loss, comprising
  a) adipose stem and regenerative cells (ADRCs) and a fat tissue, or
  b) a platelet rich plasma and a fat tissue,
wherein 1 gram of the cell-enriched fat graft comprises:
  ADRCs in a number ranging from about 10K cells to about 5 million cells, or
  the platelet rich plasma in a volume ranging from 0.001 mL to 0.9 mL.

In some embodiments of the invention graft, optionally in combination with any or all the various embodiments graft disclosed herein, the ADRCs and the fat tissue are provided in situ, and the cell-enriched fat graft is generated by mixing in-situ an amount of the ADRCs and an amount of the fat tissue prior to use.

In some embodiments of the invention graft, optionally in combination with any or all the various embodiments graft disclosed herein, the ADRCs are enzymatically extracted in situ from an adipose tissue, and the fat tissue is cleaned in situ.

In some embodiments of the invention graft, optionally in combination with any or all the various embodiments graft disclosed herein, the ADRCs are enzymatically extracted in situ and the fat tissue is collected and cleaned in situ from a liposuctioned tissue.

In some embodiments of the invention graft, optionally in combination with any or all the various embodiments graft disclosed herein, 1 mL of the cell-enriched fat graft comprises:

about 0.1 mL to about 0.9 mL the ADRCs and about 0.9 mL to about 0.1 mL fat tissue, or about 0.1 mL to about 0.9 mL the platelet rich plasma and about 0.9 mL to about 0.1 mL fat tissue.

DETAILED DESCRIPTION OF THE INVENTION

Definitions

Figure 1:
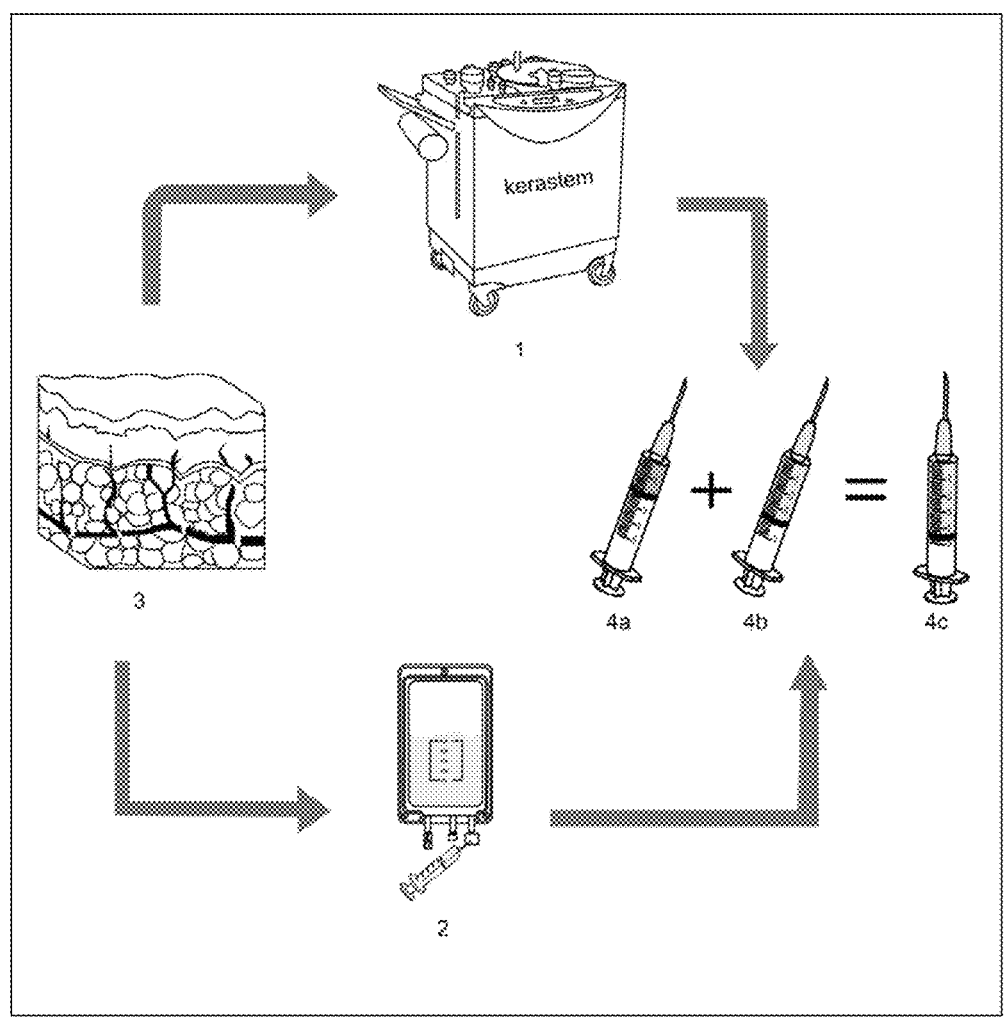
FIG. 1 shows an exemplary scheme of an embodiment of the method of hair growth and restoration of invention.

As used herein, the term tissue generally refers to tissue of an mammal such as human being. The tissue can be any kind. In some embodiments, the tissue can be a fat tissue. As used herein, the term "fat" is used interchangeably with the term "adipose".

As used herein, the term "adipose stem and regenerative cells (ADRCs)" refers to any progenitor cells for hair follicle or hair follicle niche formation, stimulation or regeneration under proper physiological conditions (e.g., the subcutaneous area region of the scalp being an area bearing hair or cilia). Examples of such ADRCs include, but are not limited to, mononuclear cells, endothelial cells, endothelial precursor cells, pericytes, and tissue specific macrophage.

As used herein, the term "enzymatically extracted" using an enzyme or enzyme(s) to extract adipose stem or regenerative cells from adipose tissue. The enzyme can be a combination of specific and non-specific proteases in addition to collagenases. An example of enzymatically extracting adipose stem cell or regenerative cells is described in U.S. patent application Ser. No. 12/771,985, the teaching of which is incorporated herein in its entirety by reference.

The term "effective", as used herein, refers to a statistically significant, measurable change of a condition in hair growth or restoration using the cell-enriched ADRCs disclosed herein as compared with the condition in hair growth or restoration without using the cell-enriched ADRCs of invention. Such effectiveness can be gauged in clinical trials as well as animal studies. Such a statistically significant, measurable, and positive change of a condition in in hair growth or restoration using the cell-enriched ADRCs disclosed herein as compared with the condition in hair growth or restoration without using the cell-enriched ADRCs of invention is referred to as an "improved condition".

As used herein, the term "significantly" or "significant" shall mean statistically significant.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Cell-Enriched Fat Graft

In an aspect of the present invention, it is provided a cell-enriched fat graft for hair growth or cilia restoration or prevention of hair loss or cilia loss, comprising a) adipose stem and regenerative cells (ADRCs) and a fat tissue, or b) a platelet rich plasma and a fat tissue, wherein 1 gram of the cell-enriched fat graft comprises:

ADRCs in a number ranging from about 10K cells to about 5 million cells, or the platelet rich plasma in a volume ranging from 0.001 mL to 0.9 mL.

In some embodiments of the invention graft, optionally in combination with any or all the various embodiments graft disclosed herein, the ADRCs and the fat tissue are provided in situ, and the cell-enriched fat graft is generated by mixing in-situ an amount of the ADRCs and an amount of the fat tissue prior to use.

In some embodiments of the invention graft, optionally in combination with any or all the various embodiments graft disclosed herein, the ADRCs are enzymatically extracted in situ from an adipose tissue, and the fat tissue is cleaned in situ.

In some embodiments of the invention graft, optionally in combination with any or all the various embodiments graft disclosed herein, the ADRCs are enzymatically extracted in situ and the fat tissue is collected and cleaned in situ from a liposuctioned tissue.

In Situ Fat Graft

As used herein, the term "in-situ" shall mean autologous tissue being taken from a patient or user using the invention method or kit, being subjected to enzymatic extraction using device 1 (FIG. 1) to generate ADRCs and regenerative cells (or platelet rich plasma), and using the ADRCs and regenerative cells or platelet rich plasma obtained therefrom to combine with autologous fat tissue cleaned again in-situ using device 2 (FIG. 1) to form a cell-enriched fat graft of invention for use for hair or cilia growth or prevention of loss thereof, all within a single procedure using the method of invention. Using in-situ generated ADRCs and regenerative cells or platelet rich plasma, and fat tissue is advantageous in that it avoids issues of ADRCs and regenerative cells or platelet rich plasma, and fat tissue obtained in other ways, such as death to the cells and exposure to immunogenic environment or materials long to prolonged preservation measures to take to preserve the ADRCs and regenerative cells or platelet rich plasma, and fat tissue. An example of device 1 is shown in FIG. 1, where collected adipose tissue is subject to enzymatic extraction to extract adipose stem and regenerative cells. With regard to device 2, still referring to FIG. 1, some embodiments of device 2 are described in WO2010127310 A1 and U.S. Patent Application No. 62/015,259, the teachings of which are incorporated herein in their entirety by reference.

Cell-Enriched Fat Graft

In one aspect of the present invention, it is provided a cell-enriched fat graft for hair growth or cilia restoration or prevention of hair loss or cilia loss. The cell-enriched fat graft comprises a) adipose stem and regenerative cells (ADRCs) and a fat tissue, or b) a platelet rich plasma and a fat tissue, wherein 1 mL of the cell-enriched fat graft comprises:

ADRCs in a number ranging from about 10K cells to about 5 million cells, or the platelet rich plasma in a volume ranging from 0.001 mL to 0.9 mL.

In some embodiments of the invention fat graft, optionally in combination with any or all of the various embodiments disclosed herein, the ADRCs and the fat tissue are provided in situ, and the cell-enriched fat graft is generated by mixing in-situ an amount of the ADRCs and an amount of the fat tissue prior to use.

In some embodiments of the invention fat graft, optionally in combination with any or all of the various embodiments disclosed herein, the ADRCs are enzymatically extracted in situ from an adipose tissue, and the fat tissue is cleaned in situ.

In some embodiments of the invention fat graft, optionally in combination with any or all of the various embodiments disclosed herein, the ADRCs are enzymatically extracted in situ and the fat tissue is collected and cleaned in situ from a liposuctioned tissue.

Liposuction is a common procedure for weight loss, and can be readily appreciated by a person of ordinary skill in the art. For the sake of concise description of invention, detailed description of liposuction is left out.

The graft of invention is obtained by a process (Puregraft) performed via membrane filtration and requires no mechanical equipment such that it is a gentle but efficient filtration, which removes 97% of contaminants. Additionally, the in-situ process of invention is a passive fluid flow facilitated by gravity and avoid excessive mechanical forces which affect tissue viability. Indeed, independent study demonstrates increased graft retention with Puregraft compared to centrifuge in a long-term follow up (average 17 months) study, which shows that in mid-face fat grafts (N=26 patients) by 3D Volumetric Measurements (Vectra), Puregraft retention was about twice of the graft by centrifuge in subset of population Age <50 years old (see, David J. Gerth, et al., Long-Term Volumetric Retention of Autologous Fat Grafting Processed With Closed-Membrane Filtration, David J. Gerth, Bethany King, Lesley Rabach, Robert A. Glasgold and Mark J. Glasgold. Aesthetic Surgery Journal published online 15 Jul. 2014).

It is noteworthy that traditional fat transfer process is not a concurrent procedure such that it is not an in-situ process.

An example of the in-situ process of invention has the following advantageous features:

intuitive process requires <15 minutes; the adipose tissue harvested and cleaned thereby would be ready for use, multiple sizes span 30-850 mL of tissue; which allows for preparing fat graft of variable sizes for single use (see below), and single-use, closed-system processing such that it is a small liposuction (small volume liposuction); which avoids potential contamination introduced by non-single use procedures, additional injury and/or death of the fat tissue by non-single use procedures, and potential immunogenicity by dead tissue and potential contamination caused by non-single use procedures.

A separate independent study by Zhu M, et al. showed that the in-situ process (Puregraft) described herein results in a 97% cleaner fat graft, and also importantly, the in-situ process described herein does not remove growth factors (see, Zhu et al., Comparison of three different fat graft preparation methods: gravity separation, centrifugation, and simultaneous washing with filtration in a closed system. Plast Reconst Surg 2013; 131(4): 873-80).

Comparison studies comparing the fat graft of invention (Puregraft) versus other commercial fat grafts are summarized below in Table 1. It is clear that fat graft of invention

TABLE 1

|  | *Puregraft | Strainer | Gravity | Revolve | LipiVage | Centrifuge |
| --- | --- | --- | --- | --- | --- | --- |
| Removal of Contaminants | High | Low | Low | Medium | Low | Medium |
| Amount of Tissue Trauma | Low | Low | Low | Low | Medium | High |
| Closed-System Design | Yes | No | Yes | Yes | Yes | No |
| Speed to Process 250 mL | <15 min | 30-45 min | 20-30 min | <15 min | 30 min | 30-45 min |
| Ease of Use | High | Low | High | High | Medium | Low |
| Tissue Volume Capabilities | Up to 850 mL* | No Limit | Variable | Up to 400 mL | 8-25 mL | 30 mL/cycle |

*Puregraft 50 handles 30-50 mL tissue/cycle. Puregraft 250 handles 50-250 mL tissue/cycle. Puregraft 850 handles 200-850 mL tissue/cycle.

The cell-enriched ADRCs of invention can have variable cell counts. Generally, the cell-enriched fat graft of invention can have cell counts from about 10K cells/gram to about 5 million cells/gram. Some exemplary cell count ranges (per gram of fat graft of invention) are:

from about 10K to about 5 million cells, about 4 million cells, about 3 million cells, about 2 million cells, about 1 million cells, about 900K cells, about 750K cells, about 500K cells, about 250K cells, about 100K cells, about 90K cells, about 75K cells, about 50K cells, or about 25K cells;

from about 25K to about 5 million cells, about 4 million cells, about 3 million cells, about 2 million cells, about 1 million cells, about 900K cells, about 750K cells, about 500K cells, about 250K cells, about 100K cells, about 90K cells, about 75K cells, or about 50K cells;

from about 50K to about 5 million cells, about 4 million cells, about 3 million cells, about 2 million cells, about 1 million cells, about 900K cells, about 750K cells, about 500K cells, about 250K cells, about 100K cells, about 90K cells, or about 75K cells;

from about 75K to about 5 million cells, about 4 million cells, about 3 million cells, about 2 million cells, about 1 million cells, about 900K cells, about 750K cells, about 500K cells, about 250K cells, about 100K cells, or about 90K cells;

from about 90K to about 5 million cells, about 4 million cells, about 3 million cells, about 2 million cells, about 1 million cells, about 900K cells, about 750K cells, about 500K cells, about 250K cells, or about 100K cells;

from about 100K to about 5 million cells, about 4 million cells, about 3 million cells, about 2 million cells, about 1 million cells, about 900K cells, about 750K cells, about 500K cells, or about 250K cells;

from about 200K to about 5 million cells, about 4 million cells, about 3 million cells, about 2 million cells, about 1 million cells, about 900K cells, about 750K cells, about 500K cells, or about 250K cells;

from about 500K to about 5 million cells, about 4 million cells, about 3 million cells, about 2 million cells, about 1 million cells, about 900K cells, or about 750K cells;

from about 750K to about 5 million cells, about 4 million cells, about 3 million cells, about 2 million cells, about 1 million cells, or about 900K cells;

from about 900K to about 5 million cells, about 4 million cells, about 3 million cells, about 2 million cells, or about 1 million cells; or from about 1 million to about 5 million cells, about 4 million cells, about 3 million cells, or about 2 million cells.

In certain embodiments, the cell count ranges (per gram of fat graft of invention) can be about 10K cells, 20K cells, 50K cells, 75K cells, 80K cells, 90K cells, 100K cells, 200K cells, 250K cells, 300K cells, 350K cells, 400K cells, 450K cells, 500K cells, 550K cells, 600K cells, 650K cells, 700K cells, 750K cells, 800K cells, 850K cells, 900K cells, 950K cells, 1 million cells, 2 million cells, 3 million cells, 4 mill cells, 5 million cells. In certain other embodiments, the cell count ranges (per gram of fat graft of invention) can be lower than 10K cells or higher than 5 million cells.

The amount of the fat graft to use is also an important factor to make the method of hair growth of invention effective, which is described in more detail below.

Additionally, the relative ratio of the stem and regenerative cells or platelet rich plasma from device 1 and the fat obtained from device 2 also plays an important role in the results of hair growth or cilia restoration. The stem and regenerative cells in the fat graft of invention helps generate near term hair growth or cilia restoration while the fat from device 2 helps sustained hair growth or cilia restoration. As such, a higher relative amount of the stem and regenerative cells in the fat graft of invention helps generate near term hair growth or cilia restoration while a higher relative amount of the fat from device 2 helps sustained hair growth or cilia restoration.

The relative ratio of the stem and regenerative cells or platelet rich plasma from device 1 and the fat obtained from device 2 can vary. For example, of 1 mL graft of invention, the ratio of the stem and regenerative cells or platelet rich plasma from device 1 to the fat obtained from device 2 can be from about 0.1 to about 0.9 or from about 0.9 to about 0.1, e.g., about 0.1 to about 0.9, about 0.2 to about 0.8, about 0.3 to about 0.7, about 0.4 to about 0.6, about 0.5 to about 0.5, about 0.6 to about 0.4, about 0.7 to about 0.3, about 0.8 to about 0.2, or about 0.9 to about 0.1.

Method of Hair Growth

In another aspect of the present invention, it is provided a method for hair growth, which method comprising
preparing a cell-enriched fat graft, and
injecting into the subcutaneous space of an area of a subject in need thereof a cell-enriched fat graft to cause hair growth or cilia restoration or to prevent hair loss or cilia loss.

In some embodiments of the invention method, optionally in combination with any or all the various embodiments method disclosed herein, the cell-enriched fat graft comprises
a) adipose stem and regenerative cells (ADRCs) and a fat tissue, or
b) a platelet rich plasma and a fat tissue.

In some embodiments of the invention method, optionally in combination with any or all the various embodiments method disclosed herein, 1 gram of the cell-enriched fat graft comprises:
ADRCs in a number ranging from about 10,000 cells to about 5 million cells, or
the platelet rich plasma in a volume ranging from 0.001 mL to 0.9 mL.

In some embodiments of the invention method, optionally in combination with any or all the various embodiments method disclosed herein, the ADRCs and the fat tissue are provided in situ, and the cell-enriched fat graft is generated by mixing in-situ an amount of the ADRCs and an amount of the fat tissue prior to use.

In some embodiments of the invention method, optionally in combination with any or all the various embodiments method disclosed herein, the ADRCs are enzymatically extracted in situ from an adipose tissue, and the fat tissue is cleaned in situ.

In some embodiments of the invention method, optionally in combination with any or all the various embodiments method disclosed herein, the ADRCs are enzymatically extracted in situ and the fat tissue is collected and cleaned in situ from a liposuctioned tissue.

In some embodiments of the invention method, optionally in combination with any or all the various embodiments method disclosed herein, the area of a subject is ear drum or intestine.

In some embodiments of the invention method, optionally in combination with any or all the various embodiments method disclosed herein, preparing comprises:
measuring the size of the area of the subject in need of hair growth or cilia restoration, determining a cell count in the cell-enriched fat graft,
determining an amount of the cell-enriched fat graft of the cell count to generate effective hair growth or cilia restoration in the area.

In some embodiments of the invention method, optionally in combination with any or all the various embodiments method disclosed herein, the subject is a human being.

The cell-enriched fat graft of the various embodiment is as described above.

A Kit

In another aspect of the present invention, it is provided a kit for providing a cell-enriched fat graft in situ, which kit comprising
an adipose stem and regenerative isolation device; and an adipose tissue cleaning device, wherein the adipose stem and regenerative cells (ADRCs) isolation device comprises a mechanism to enzymatically extract ADRCs from an adipose tissue, and wherein the adipose tissue cleaning device comprises a mechanism to collect and clean an adipose tissue without causing injury to the adipose tissue.

In some embodiments of the invention kit, optionally in combination with any or all the various embodiments kit disclosed herein, the adipose tissue cleaning device comprises a soft bag comprising soft compartments.

The kit system can be used to collect multiple types of tissue/fluid not just adipose and fluids removed via the liposuction process in a closed manner.

EXAMPLES

The following examples illustrate the present invention and shall not be construed to limit the scope of the present invention.

Example 1

Hair Growth on Scalp Using an Embodiment of Fat Graft of Invention

General

Examples of hair growth on scalp using a cell-enriched fat graft of invention according to the general protocol described above were carried out. Described below is an exemplary procedure for hair growth.

A novel method using a series of unique medical devices that when combined and injected into the patients—grow hair and thus retard further hair loss. Novel device 1 (FIG. 1) is used to enzymatically extract adipose stem and regenerative cells in real time. Adipose stem and regenerative cells can be replaced by platelet rich plasma. Adipose tissue is cleaned in Novel device 2 (FIG. 1) in real time. The output of novel device 1 and novel device 2 is combined using 1 ml of output from device 1 combined with an amount of fat from novel device 2 that is derived from the following formula: square centimeter of scalp to be treated×0.1×2, that is, in 1 square centimeter of scalp, a total of 0.2 mL combined material from device 1 (enzymatically extracted stem and regenerative cells or platelet rich plasma) and device 2 (fat). The combined material is mixed and injected into a patient's subcutaneous adipose plane in the scalp at approximately 0.1 ml per square centimeter.

An example of the process disclosed herein is shown in FIG. 1. Referring to FIG. 1, device 1 is an adipose stem and regenerative cells isolation device, device 2 is an adipose tissue cleaning device. Both device 1 and device 2 are as defined above. Liposuctioned tissue 3 is an autologous adipose tissue mass obtained by a liposuction procedure on the test subject. 35 mL of the liposuctioned tissue is taken to undergo ADRCs and regenerative cells isolation (also referred to as abstraction) via device 1 to generate ADRCs and regenerative cells 4a, and 65 mL of the liposuctioned tissue is taken to undergo cleaning procedures via device 2 to generate fat tissue 4b. 4a and 4b are combined to generate cell-enriched fat graft 4c. an amount of 4c is injected in the subcutaneous space of the subject (FIG. 2).

Figure 2:
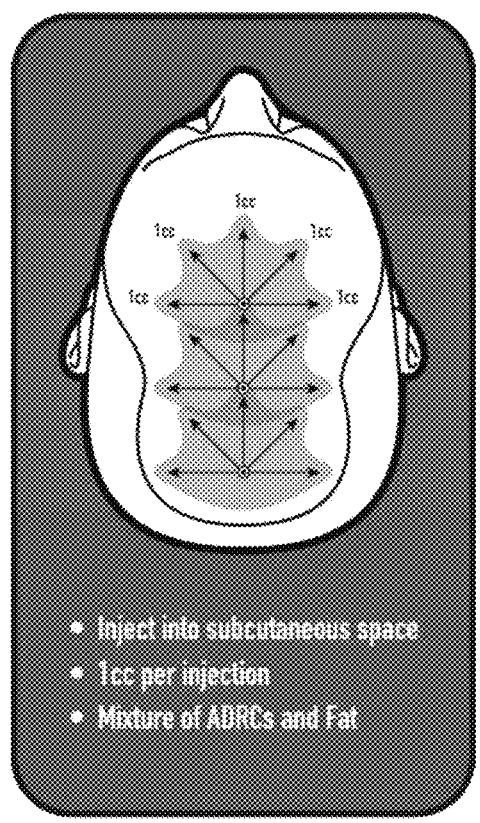
FIG. 2 shows an example pattern of injection of an embodiment of the cell-enriched fat graft of invention injected in the subcutaneous space of scalp of a subject.

FIG. 2 shows that the "cell enriched fat graft" 4c as described in this example is injected in the subcutaneous space (FIG. 2, not intended to represent the exact recommended volume).

Figure 3:
FIG. 3 shows the results of 60 day post treatment of a test subject using an example of cell-enriched fat graft of invention.

FIG. 3 shows the results of 60 day post treatment of a test subject. The data is summarized in Table 2 below.

TABLE 2

|  | Hair Counts per cm$^2$ | Hair Density per cm$^2$ | Anagen % | Telogen % | Cumm. Thickness per cm$^2$ |
|---|---|---|---|---|---|
| Average baseline | 321.7 | 311.5 | 47.1% | 52.9% | 16.3 |
| Average 6-month data | 340 | 330 | 36.1% | 63.9% | 17 |
| Average 6-month Δ% | 6% | 6% | −23% | 21% | 7% |

Example 2

Studies on Hair Follicle Stimulation by Stromal Vascular Fraction Enhanced Adipose Transplantation Introduction: There is an emerging interest in the role of adipose tissue in the context of the complex hair growth cycle. This interest has been elevated as a number of investigators have previously reported a positive change in hair growth subsequent to subcutaneous fat grafting. Our group aim is to further clinically explore this relationship.

Figure 4:
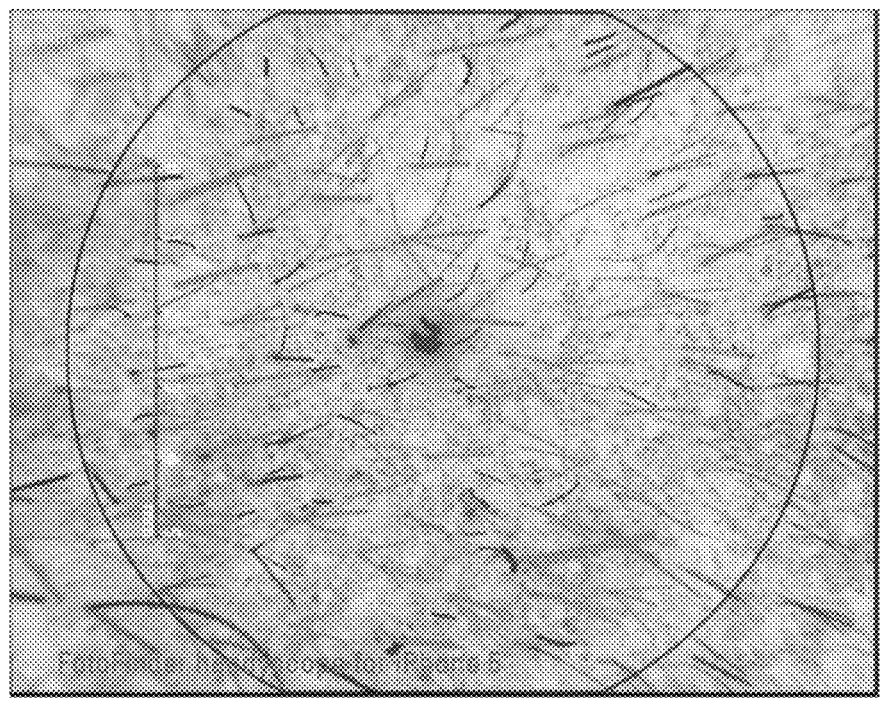
FIG. 4 shows trichoscan analysis of hair count, hair density, anagen/telogen rates, and cumulative hair thickness.

Method: Nine healthy patients (eight men and one woman) with male and female pattern hair loss were treated by autologous fat transplantation, enriched with stromal vascular fraction (SVF) to the scalp. All nine patients underwent a routine syringe-based liposuction and adipose was separated into two aliquots. One aliquot was purified using a commercially available fat filtration system (Puregraft®, Puregraft Technologies) and set aside. The remaining tissue was digested to obtain concentrated stromal vascular fraction cells (SVF, Cytori Therapeutics). The SVF was mixed with the purified fat tissue and injected into the subcutaneous fatty layer of the affected scalp using fat grafting cannula. Patients are followed for safety and tolerability and for monitoring differences in hair growth. To track progress, we employ global photography and trichoscan analysis using a handyscope with micro-tattoos (Fotofinder). Trichoscan analysis allows us to quantitatively track the following parameters: hair count, hair density, anagen/telogen rates (48 hours later), and cumulative hair thickness (FIG. 4). Follow-up is at 6 weeks, 12 weeks, and 24 weeks.

Hair count, hair density, anagen/telogen rates, and cumulative hair thickness can be analyzed by Trichoscan analysis (FIG. 4).

Results: Our early experience demonstrates an encouraging trend in 6-week trichoscan parameters, showing an average of 40% increase in hair count along with a 41% increase in cumulative hair thickness in the first two patients from the cohort. 6-month data on all 9 patients will be presented at the meeting.

Conclusion: The authors intend to present the following preliminary results for 9 patients: 6-month safety and hair growth data as well as review the cumulative experience with scalp stem cell enriched fat grafting in the treatment of alopecia.

We claim:

1. A method for hair growth, comprising
preparing a cell-enriched fat graft in-situ, and
injecting into the subcutaneous space of an area of a subject in need thereof a cell-enriched fat graft to cause hair growth or cilia restoration or to prevent hair loss or cilia loss, wherein the cell-enriched fat graft comprises a) concentrated stromal vascular fraction cells comprising adipose stem and regenerative cells (ADRCs) and a purified fat tissue, or
b) a platelet rich plasma and a purified fat tissue; and
wherein the purified fat tissue is purified using a commercially available fat filtration system, and
wherein preparing the cell-enriched fat graft in-situ does not subject cells to culturing and centrifuging.

2. The method of claim 1, wherein 1 gram of the cell-enriched fat graft comprises:
ADRCs in a number ranging from about 10,000 cells to about 5 million cells, or
the platelet rich plasma in a volume ranging from 0.001 mL to 0.9 mL.

3. The method of claim 1, wherein the ADRCs and the fat tissue are provided in situ, and the cell-enriched fat graft is generated by mixing in-situ an amount of the ADRCs and an amount of the fat tissue prior to use.

4. The method of claim 3, wherein the ADRCs are enzymatically extracted in situ from an adipose tissue, and the fat tissue is cleaned in situ.

5. The method of claim 4, wherein the ADRCs are enzymatically extracted in situ and the fat tissue is collected and cleaned in situ from a liposuctioned tissue.

6. The method of claim 1, wherein the area of a subject is ear drum or intestine.

7. The method of claim 1, wherein preparing comprises:
measuring the size of the area of the subject in need of hair growth or cilia restoration, determining a cell count in the cell-enriched fat graft,
determining an amount of the cell-enriched fat graft of the cell count to generate effective hair growth or cilia restoration in the area.

8. The method of claim 1, wherein the subject is a human being.

* * * * *